(12) United States Patent  (10) Patent No.: US 7,777,696 B2
Rohner et al.                (45) Date of Patent: Aug. 17, 2010

(54) DISPLAY ASSOCIATED WITH A TREATMENT DEVICE FOR DENTAL MATERIAL

(75) Inventors: Gottfried Rohner, Alstatten (CH); Robert Gruenenfelder, Eschen (LI)

(73) Assignee: Ivoclar Vivadeal AG, Schaan (LI)

( * ) Notice: Subject to any disclaimer, the term of this patent is extended or adjusted under 35 U.S.C. 154(b) by 1265 days.

(21) Appl. No.: 11/318,780

(22) Filed: Dec. 27, 2005

(65) Prior Publication Data

US 2007/0065769 A1   Mar. 22, 2007

(30) Foreign Application Priority Data

Sep. 20, 2005   (DE) .................. 10 2005 044 882

(51) Int. Cl.
  *G09G 3/28* (2006.01)
(52) U.S. Cl. .............. 345/72; 345/83; 345/88; 433/29; 433/215; 348/66
(58) Field of Classification Search ............ 345/32, 345/204, 549, 72, 83, 88; 433/26, 27, 215, 433/29; 700/98; 382/162, 164; 348/83; 349/97, 106
  See application file for complete search history.

(56) References Cited

U.S. PATENT DOCUMENTS

| 5,295,833 | A |   | 3/1994 | Chihiro et al. |
| 6,089,740 | A |   | 7/2000 | Forehand et al. |
| 6,117,285 | A |   | 9/2000 | Welch et al. |
| 6,118,521 | A |   | 9/2000 | Jung et al. |
| 6,382,967 | B1 | * | 5/2002 | Rohner et al. ............... 433/29 |
| 2001/0023056 | A1 |   | 9/2001 | Gruenenfelder et al. |
| 2005/0042572 | A1 |   | 2/2005 | Katsuda et al. |

FOREIGN PATENT DOCUMENTS

| DE | G 81 34 121.0 U1 | 10/1983 |
| DE | 195 20 765 A1 | 12/1995 |
| DE | 197 54 077 A1 | 6/1999 |
| DE | 20 2005 005529 U1 | 9/2006 |

\* cited by examiner

*Primary Examiner*—Abbas I Abdulselam
(74) *Attorney, Agent, or Firm*—John C. Thompson; Alan S. Korman; Sandra J. Thompson

(57) ABSTRACT

A display associated with a treatment device for dental material, with which at least one operating state of the device can be displayed. The display is a function of the operating state of the device. The display shows different operating states of the treatment device exclusively with the aid of color signals, whereby each color is associated with an operating state of the device.

22 Claims, 6 Drawing Sheets

DISPLAY ASSOCIATED WITH A TREATMENT DEVICE FOR DENTAL MATERIAL

CROSS-REFERENCE TO RELATED APPLICATIONS

This application claims foreign priority benefits under 35 U.S.C. 119 from German patent application Ser. No. 10 2005 044 882.8 filed Sep. 20, 2005.

TECHNICAL FIELD

The invention relates generally to a treatment device for dental material, and more particularly to a display associated with such a device.

BACKGROUND OF THE INVENTION

These types of treatment devices for dental material include stationary devices, such as polymerization devices, which operate with light and/or heat and are used for polymerizing a dental restoration material from a polymerizable plastic. However, these types of treatment devices also include compression ovens or burning ovens or kilns. These types of dental devices or dental material treatment devices generally have a program or software control, which controls the various operating states, such as pre-compression or post-compression with burning ovens or kilns, the heating or cool-down phase in burning oven or kilns, or different phases of the dispersion of the polymerization radiation in polymerization devices.

In larger dental laboratories, usually many corresponding dental devices are provided. In this connection, it is known to signal the corresponding operating state with an acoustic or also an optical signal.

One recent example is provided disclosed in US 20010023056 A1. With this design of a program-controlled dental device, the end of the firing cycle is signaled via a light diode and a buzzer, both of which are mounted in an operator panel below and in front on the burning oven or kiln. An acoustic alarm is provided when an operator is to be notified of the end of a process. Often, however, such an alarm does not make possible the association to the device emitting the alarm, and, therefore, it does not make possible the quick detection of the actual operating state.

In addition, it has been proposed to signal the operating temperature, for example of a specialized burning oven or kiln, via so-called teleindication, or also to signal the expected time until the end of the firing cycle via characters. However, it was shown that a plurality of such digitally-represented information only detects or processes a minimal number of burning ovens or kilns, for example three kilns. If a plurality of kilns, for example 20 kilns, or also other dental treatment devices, are operated together, it is practically impossible to detect the digitally prepared information from a distance; especially with two different and similar pieces of information, a mistake can occur. These types of digital displays are relatively expensive to realize, in particular if, despite a projecting arrangement, they are to be protected.

A further disadvantage of such displays is that their visibility depends greatly on ambient illumination. For example, white characters on a black background are relatively difficult to recognize in daylight, while orange or red characters are relatively difficult to recognize where illumination is with incandescent light. Thus, such tele-indicators are not widely used, and it was already proposed to rely on acoustic signals, which are different depending on the burning oven or kiln or other dental device. On the other hand, such signals are easily mistaken for an alarm, and the alarm function is limited by a plurality of other acoustic signals that serve merely for information purposes.

OBJECTS AND SUMMARY OF THE INVENTION

Therefore, the present invention is based on the object of making a treatment device for dental material that is improved with regard to its acceptance in dental laboratories work or larger dental practices and still offers favorable information content despite the reduced costs.

With the association of different operating states to color signals according to the present invention, which signal the respective operating state, it was achieved in a surprisingly simple manner that the operator always is informed about a plurality of dental devices and their operating state. With one look, he can gather information, even for 20 dental devices for example, whether his intervention is necessary or whether he first can perform other work.

According to the present invention, it is especially favorable if at least one display panel is provided which is equipped with multiple light diodes. For example, red, yellow, green or blue light diodes can be arranged compactly adjacent one another, and the display panel can be formed by a so-called black glass disk (acrylic glass with very fine incorporated soot particles), so that with all states of ambient light, the visibility is comparably good; however still a corresponding display is realized in a cost-effective manner.

An alarm function, for example a malfunction of the device in one operating state, can then be realized in a simple manner by looking at the related light diode, so that the operator can determine at the same time in which operating state the alarm has occurred. According to the present invention, it is particularly favorable if the display panel is holohedrally illuminated, but is not too small. For example it can extend over a surface of 2 square centimeters, or also ten or even 40 square centimeters, and either in the front area of the pertaining dental device or above the dental device, depending whether the dental devices are visible from the front, which is the case for example when the dental devices are arranged in a row, or if they are arranged in the form of a field.

It is particularly favorable when additional information can be determined by the optical display of color signals via the adjustment of any light parameter, without loss of the primary information, that is, the operating state of the dental device. For example a modulation signal can be modulated easily with light diodes, which changes when nearing the respective end of the operating state. Here, one blink can be used for example, or however, also an alternating switching-on of the related light diode with high intensity and with low intensity.

It is also possible to switch on both of the associated color light diodes alternatingly upon transition between one operating state and the other operating state, and even with increasing or decreasing switching duration, so that a transition between both related operating states can be visually simulated.

Instead of the realization of light diodes, also on-the-spot, differently colored display panels can be supplied with any light source, so that they alternatingly can permit the corresponding and desired signal function. Also, it is possible to bring corresponding color surfaces into the visible range and outside of the visible range of the operator by mechanical movements, in order to make available the desired color signalization.

According to a further advantageous embodiment of the present invention, the display has at least one display panel, which is illuminated to the magnitude of multiple square centimeters.

According to a further advantageous embodiment, at least one display panel of the display changes its color as a function of the changed operating state of the treatment device.

In a further advantageous embodiment, a color change of at least one display panel of the display is realized by switching-off a light source having an emission spectrum corresponding to one color, and promptly switching on a further light source having an emission spectrum corresponding to a different color.

In a further advantageous embodiment, a light source, in particular a color-neutral light source, supplies at least one display panel with light, whereby the display panel is colored and in particular, translucent, and the light source is arranged behind the display panel.

In a further advantageous embodiment, a plurality of light sources are provided for providing displays which have at least partly different colors, and of which in particular at least two supply the same display panel.

In a further advantageous embodiment, the light source is covered by a cover that is permeable by the light emitted by the light source.

In a further advantageous embodiment, at least one display panel is kept colored and takes up a substantial part of a surface of the treatment device visible from the side or front, in particular at least two percent, preferably at least three percent and particularly preferred approximately five percent of this surface.

In a further advantageous embodiment, the display is arranged on the front side of the device and/or the display is arranged above the device and/or laterally on the device and/or on the underside of the device.

In a further advantageous embodiment, the color signals are visible constantly and/or in intervals for the duration of the respective operating state.

In a further advantageous embodiment, at least one display panel is color coated and at least two differently color-coated display panels are alternatingly visible depending on the operating state of the treatment device.

In a further advantageous embodiment, the color signals appear on at least one colored display surface, which is located in particular on a support element, which is controllably moveable as a function of the operating state.

In a further advantageous embodiment, the support element is formed by a rotating band, on which multiple colored surfaces with different colors are arranged.

In a further advantageous embodiment, the support element is formed by a rotatable disk, on which multiple colored surfaces with different colors are arranged.

In a further advantageous embodiment, the display is connected spatially with the treatment device or is connected via a cable connection or radio with the treatment device.

In a further advantageous embodiment, the device is a burning oven or kiln, or a compression oven, or a polymerization device, in particular a polymerization device that operates with light and/or heat.

DETAILED DESCRIPTION

Figure 1:
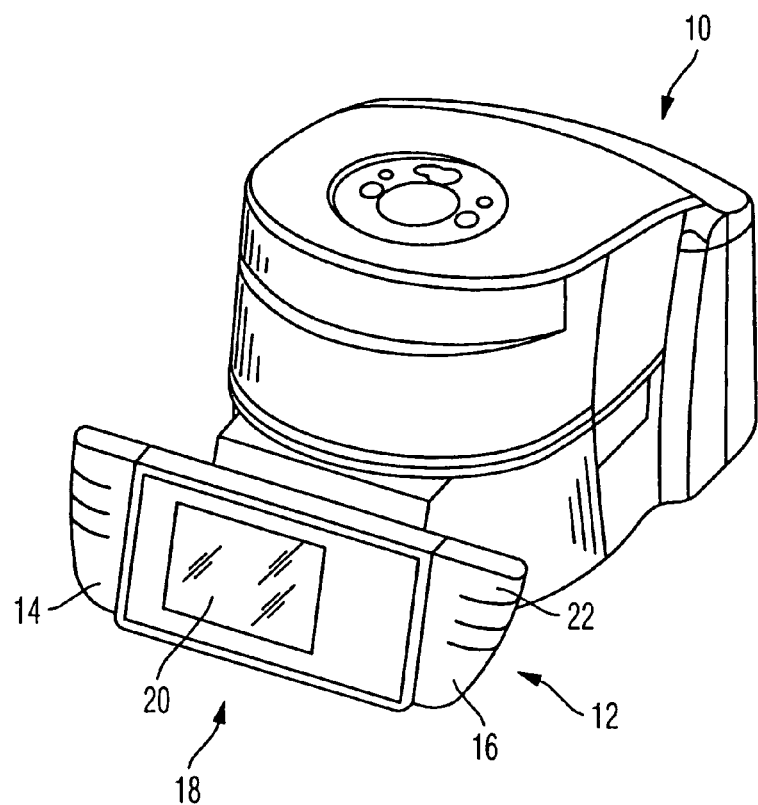
FIG. 1 is a perspective view of a first embodiment of a display associated with a treatment device for dental material, the treatment device being a burning oven or kiln assembly, the assembly having two display panels to either side of a touch screen.

FIG. 1 shows a dental material treatment device or assembly 10 in the form of a burning oven or kiln assembly. The dental material treatment device 10 has a display 12 associated therewith, which in the embodiment shown in FIG. 1 is visible from the front and also from the side. While the illustrated dental material treatment assembly is shown in the form of a burning oven or kiln, it should be realized that the display can be associated with other dental material treatment assemblies such as compression oven or a polymerization assembly which operates with light and/or heat.

Figure 4:
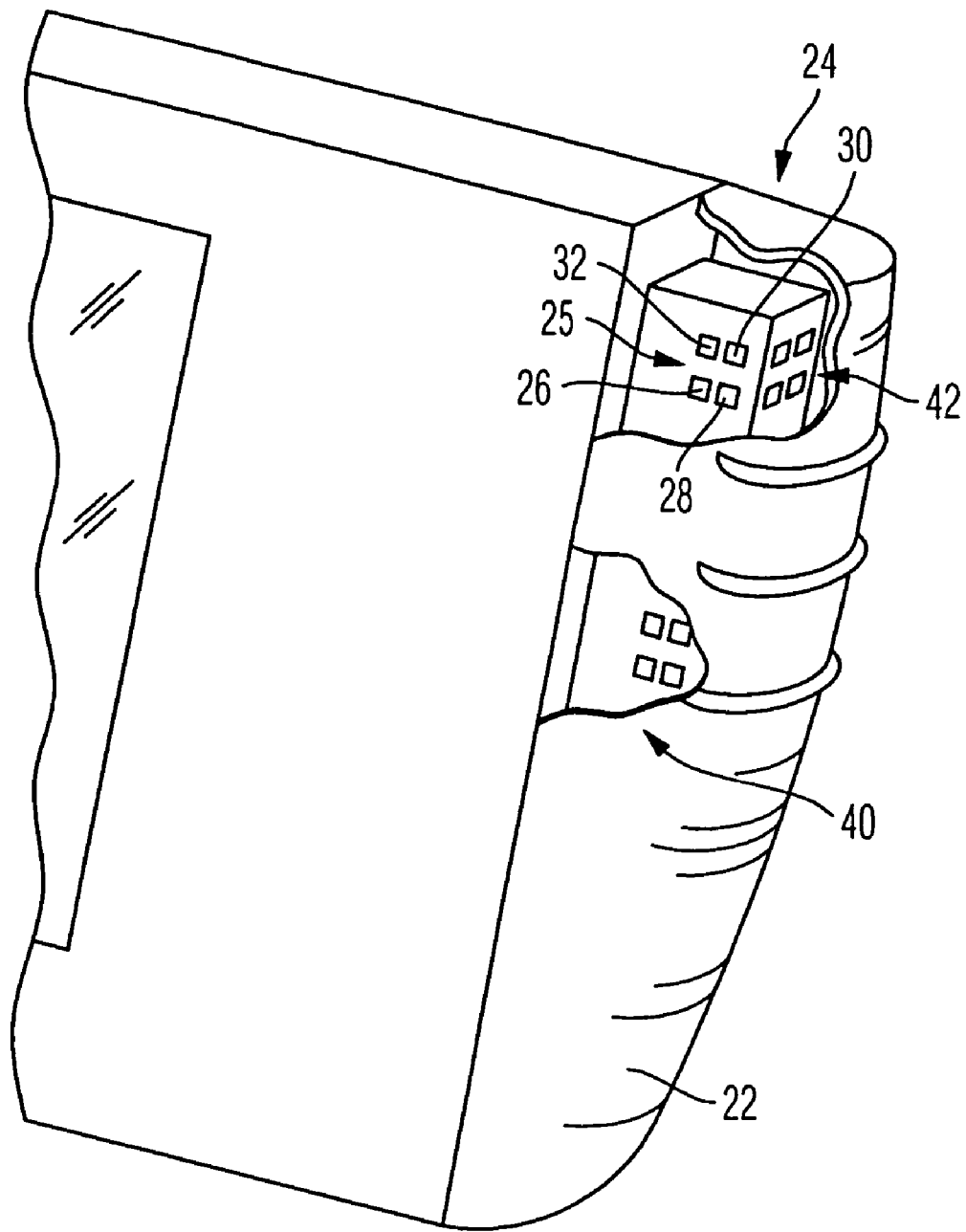
FIG. 4 is an enlarged and partially exploded representation of the apparatus shown in FIGS. 2 and 3.
Figure 5:
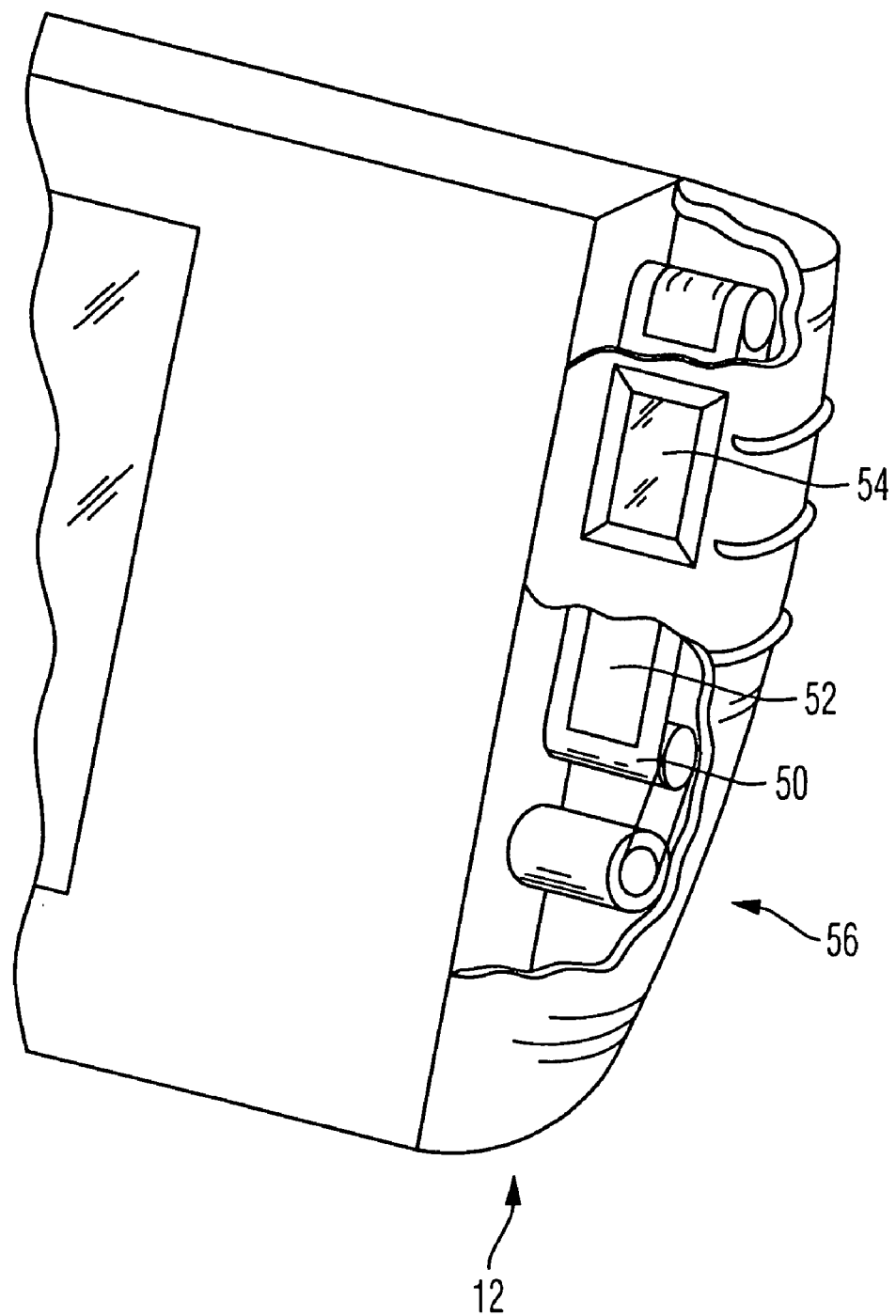
FIG. 5 is a modified embodiment in a representation according to FIG. 4.

As shown in FIG. 1, the display has two display panels 14 and 16, each of which is equipped with light diodes, as can be seen more clearly from FIG. 4 or FIG. 5. The display panels extend in the manner of ears laterally in the elongation of an operator control panel or an operator control panel 18, which is responsible for the communication between the operator and the kiln. Via the operator control panel 18, the kiln can be controlled via a display screen 20 which also functions as a touch screen 20. Information such as the burning curve, temperature, and so on are displayed on the display.

In contrast, the display panels 14 and 16 extend adjoining but not as one piece with the operator control panel 18.

In a modified embodiment of the treatment device of the present invention, which is not shown here, the display panels 14 and 16 are integrated as part of the display 12 in the operator control panel 18 and, for example, can be connected directly to the display screen 20.

Instead of the realization of light diodes, differently colored display panels can be supplied with any light source, so that they alternatingly can permit the corresponding and desired signal function. Also, it is possible to bring them into and out of the visible range of the operator by mechanical movements, in order to make available the desired color signalization The display panels 14 and 16, whose arrangement and design also can be seen well from FIGS. 2 and 3, comprise a translucent material, for example plastic. The material is neutrally colored.

It is particularly expedient for the display panels 14 and 16 to be formed as bonnets and the light sources, which provide color signals, are encased in a manner such that these are not visible, except when illuminated. According to the present invention, it is especially favorable that a clear display is permitted with good perceptibility, independent of the ambient light conditions. Each display panel has a considerable appearance surface, whereby the visible intensity of the display panels 14 and 16 of FIG. 3 are selected so that here a surface that is too small is not used. In the front view of FIG. 2, the surface amounts to 25 cm$^2$ for example, and in the side view of FIG. 3, 15 cm$^2$. In a further advantageous embodiment, at least one display panel is kept colored and takes up a substantial part of a surface of the treatment device visible from the side or front, in particular at least two percent, preferably at least three percent and particularly preferred approximately five percent of this surface. With correspondingly intense light sources, these also suffice for signalizing of colors, which is provided in a holohedral form via the display panels 14 and 16, optically representing the operating state of the treatment device 10 over a sufficiently wide distance. The color change in the display is achieved by turning off one light source with an emission spectrum and a corresponding color, and turning on a further light source with an emission spectrum corresponding to a different color.

Figure 2:
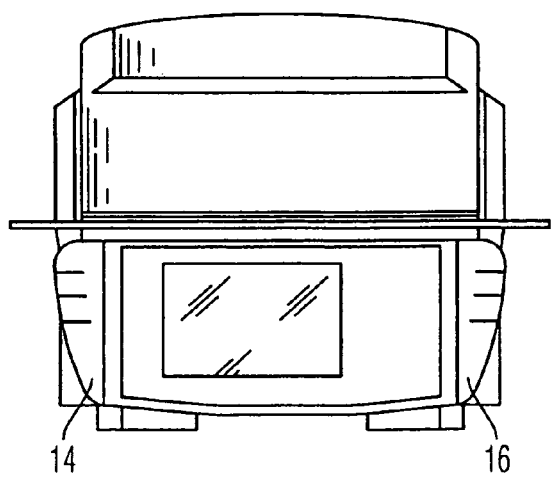
FIG. 2 is a front view of a variations of the apparatus shown in FIG. 1, the display panels being narrower than the display panels shown in FIG. 1.
Figure 3:
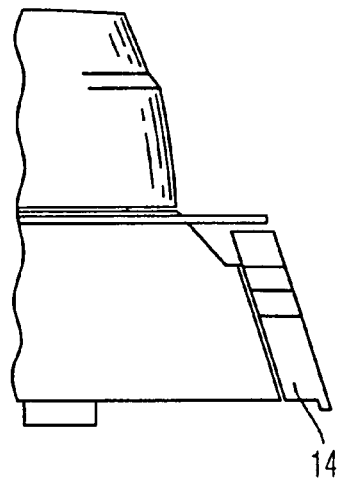
FIG. 3 is a side view of a part of the apparatus shown in FIG. 2.

In FIG. 1, an embodiment of the display panels 14 and 16 is provided in a somewhat enlarged design relative to FIG. 2. With this design, the display panels 14 and 16 are more greatly slanted in part, so that they are wider above than below. Preferably, the bonnets 22 provided there, respectively, also are rounded on the outside, as can be seen from both FIGS. 1 and 2, so that despite the projecting regions, no danger of injury exists.

According to the present invention, the material of each bonnet 22 is a transparent or translucent plastic, which has for example embedded black particles. In this manner, a diffusion effect is produced, without reducing the intensity of the light radiation, because the light radiation emitted by the light sources 24, as shown in FIG. 4, is deflected on the black particles in a known manner, so that diffusion of the light exists. In an alternative embodiment, the display panel is formed by a so-called black glass disk (acrylic glass with very fine incorporated soot particles), so that with all states of ambient light, the visibility is comparatively good; however still a corresponding display is realized in a cost-effective manner.

According to the present invention, the color presented to the operator changes depending on the operating state of the treatment device 10. For example, it is known that the heating cycle to a determined temperature point of the burning oven or kiln is represented as red/yellow. The realization of the red/yellow display can be realized by corresponding light diodes or LEDs. By way of example, as shown in FIG. 4, the light diodes are combined in fields or panels, whereby here as an example, one illumination field or light panel 25 is described. The illumination field 25 comprises one green (or blue) light diode 26, one yellow light diode 28, one red light diode 30, and one white light diode 32. If only red/yellow is to be represented, the red light diode 30 and the yellow light diode 28 are switched on. With the simultaneous switching on of these light diodes, the display panel 16 appears orange, while it is also possible to switch on the light diodes alternatingly, so that a red/yellow blinking effect is provided. The colored signals are constantly visible during their associated operating states or, alternatively, the signals are visible in intervals.

When the operating temperature is reached at which the oven can be filled, merely the green light diode 26 is switched on for example. During the burning cycle, for example the red and green light diodes 26 and 30 can be switched on alternatingly; during the cooling phase, for example, the red and white light diodes blink and when the dental materials are ready to be removed, the green light diode blinks.

It should be understood that the color signals shown here are only examples and any association of colors to the operating states is possible without departing from the invention.

While it is preferred according to the present invention to represent abruptly the change of operating states, that is, for example, to go abruptly from a yellow/red state to the red state, in a modified embodiment it is provided to show the transition visually and in this regard, by way of example, to adapt the pulse-width modulation between red and yellow light diodes 30 and 28 upon approaching the "red" operating state in such a way that more red portions are shown.

In the embodiment shown in FIG. 4, in addition to the light panel 25, a plurality of additional light panels are provided, of which two light panels 40 and 42 can be seen in FIG. 4. The light panels 25, 40, and 42 extend in a suitable manner beneath the bonnet 22, so that a holohedral display is produced.

While in FIGS. 1 through 3 the display 12 is shown with the use of self-illuminating light sources, specifically, with light diodes, it should be understood that instead of these, also any other self-illuminating light sources are realizable, such as colored laser diodes, light bulbs, including colored halogen bulbs, or also colored LCD displays, without departing from the present invention. Alternatively, also white light sources can be combined with appropriate color filters.

A modified embodiment is shown in FIG. 5, which does not include illumination means. In this embodiment, a light source, particularly a color-neutral light source, is located behind the display panel and supplies at least one display panel with light, the display panel being colored or translucent. Here, a revolving band 50 is provided, which supports different color fields 52, which are visible beneath a transparent window 54. Via a drive 56, the position of the respective field 52 can be brought to cover the window 54, so that the related field is visible as a color signal. With this solution, which can be used in good visibility conditions, the color signalization can be realized according to the present invention.

A similar embodiment of the display shown in FIG. 5 has a rotatable disk having sections of different colors located under a display window through which only a section of the disk is visible. The disk rotates to present a different colored section in the window. The different colored sections correspond to different operating states of the device.

Figure 6:
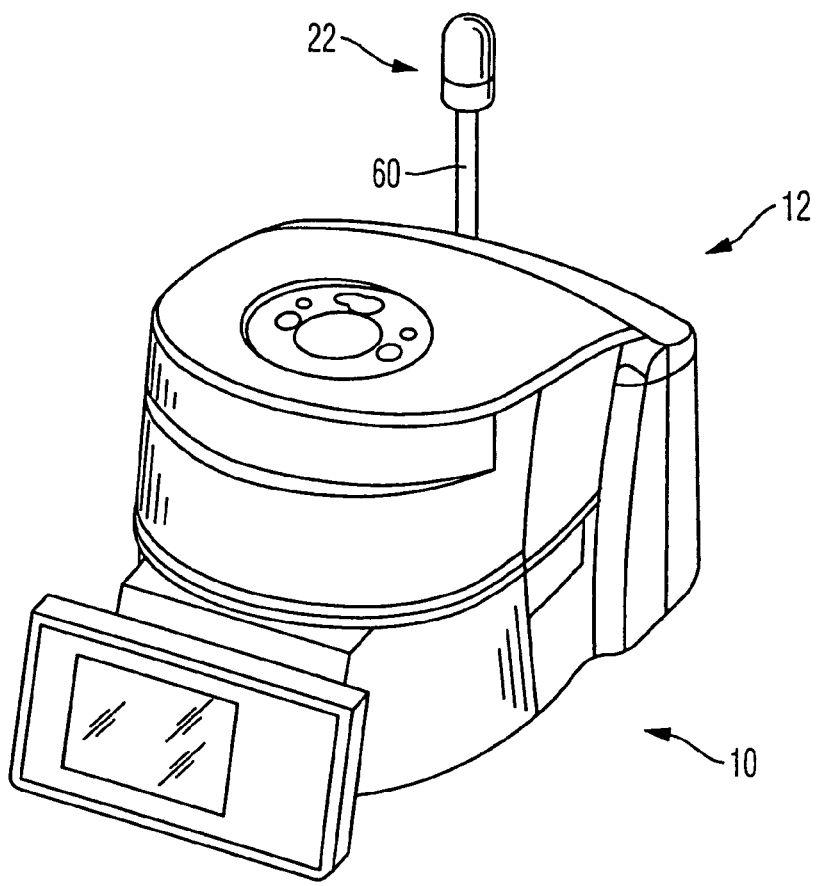
FIG. 6 is a perspective representation of a further embodiment of a display associated with a treatment device according to the present invention.

Further types of displays 12 can be seen from the additional figures. FIG. 6 shows a display 12, which is mounted above the treatment device 10 on an antenna-like rod 60. The display 12 according to FIG. 6 is visible all around and has a substantially semi-circular bonnet 22, which covers the light source or the light sources in a suitable manner. Any suitably colored light means can be accommodated here and switched on in a suitable manner for signalizing the operating states. This type of display 12 also is visible from afar, and even when a plurality of treatment devices are two-dimensionally arranged in the manner of a field, side-by-side, and the front side of the corresponding treatment device then is not necessarily visible.

Figure 7:
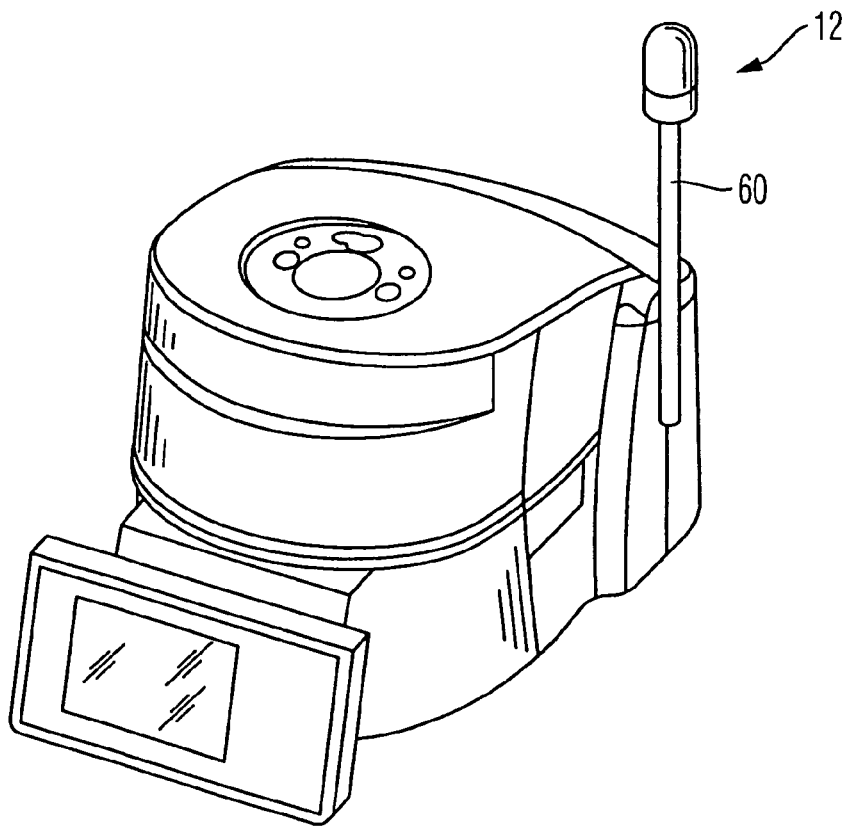
FIG. 7 is a further representation of a display associated with a treatment device of the present invention in a further embodiment.

A similar embodiment of the display is shown in FIG. 7. There, the rod 60 is mounted laterally, whereby for the visibility, the same preferences apply as with the embodiment of FIG. 6.

Figure 8:
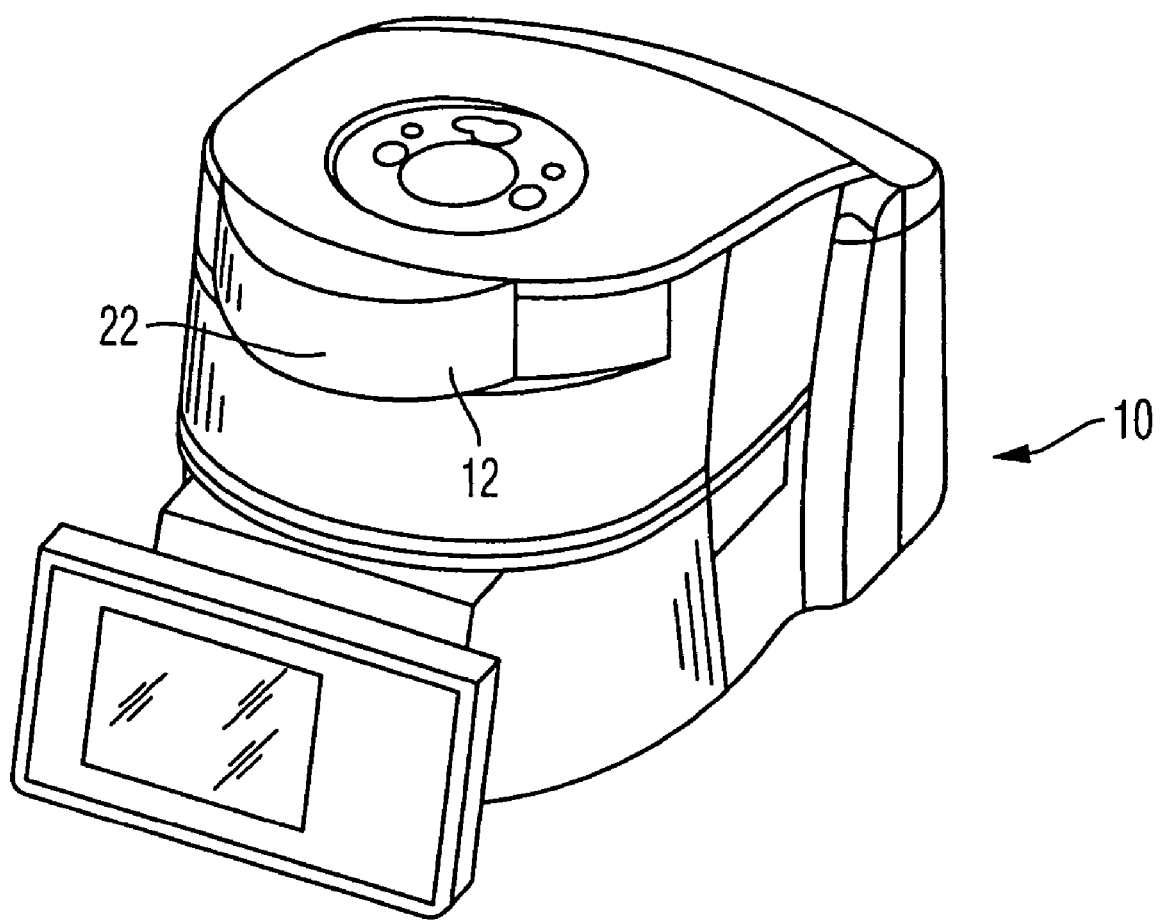
FIG. 8 is a further embodiment of a display associated with a treatment device of the present invention in a perspective representation.

A further embodiment of the display 12 of the present invention is shown in FIG. 8. With this embodiment, the front visibility is especially good; the display 12 can be recognized better from a distance than those shown in FIGS. 1 through 5. The display is mounted in the front/above on the treatment device 10 and is maintained as a large surface. It has a visible surface of 50 cm$^2$, whereby a plurality of intense light sources can be mounted there by means of the large-volume bonnet 22. Alternatively, the display can be mounted on the underside of the device and/or directly on the device laterally and/or on the front side.

It should be understood that the light effect can be increased further by mounting reflectors, which, however, are not visible through the bonnet 22.

Figure 9:
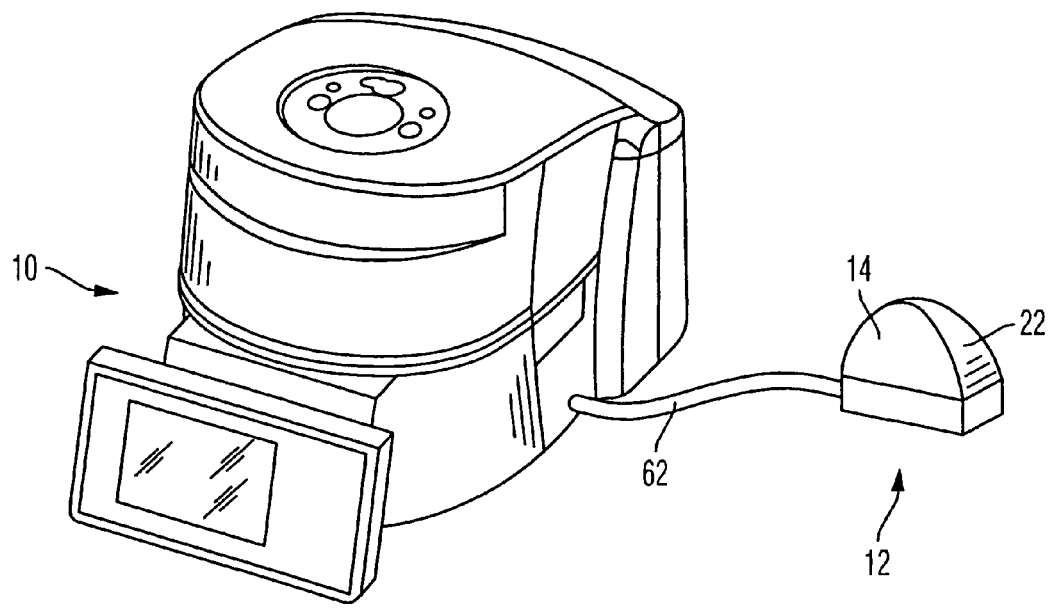
FIG. 9 is a perspective representation of a further embodiment of a display associated with a treatment device of the present invention.

FIG. 9 shows a further embodiment of a display 12 of the present invention. The embodiment shown in FIG. 9 has an arrangement of the display 12 that is spatially separated from the device 10 at a few centimeters, for example 20 cm or also 50 cm. The display 12 has a transparent or translucent bonnet 22, which forms a display panel 14 and accommodates a suitable arrangement of light sources. The supply of the light sources takes place via a cable 62, which enables the display to be placed laterally near the device 10 according to the needs of the operator, or also on the device when a better view from a distance is desired.

Figure 10:
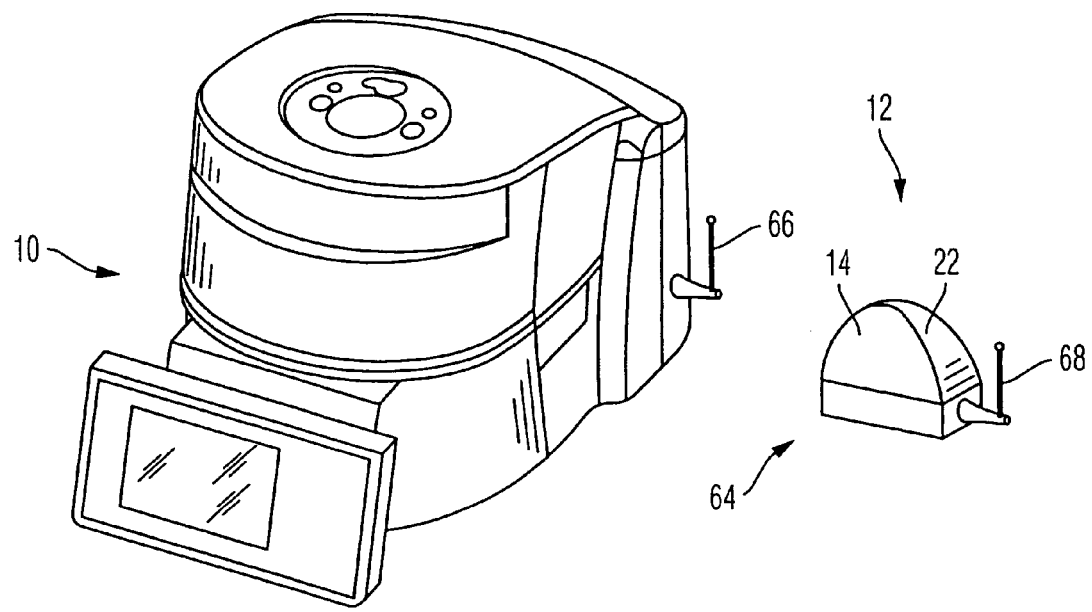
FIG. 10 is a perspective representation of a further embodiment of a display associated with a treatment device according to the present invention.

A somewhat modified embodiment of the treatment device 10 is shown in FIG. 10. Here, the cable is replaced by a radio connection 64, which has two antennae 66 and 68 for example. One antenna 66 is mounted on the device 10 and one antenna 68 is mounted on the display panel 14.

It should be understood that instead of the radio connection, also an infrared connection or any other suitable transmission of the information can be realized. This solution makes possible a still more flexible arrangement of the display 12.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A display associated with a treatment device for dental material; the display being characterized by:
   the display being a function of at least one operating state of the device,
   the display incorporating one or more display panels which display different operating states of the treatment device exclusively with the assistance of color signals, each color being associated with an operating state of the device, the color presented to the operator changing depending on the operating state of the treatment device, and
   wherein a color change of at least one display panel of the display is realized by switching off a light source having an emission spectrum corresponding to one color, and prompt switching on of a further light source having emission spectrum corresponding to a different color.

2. The display of claim 1 wherein the display has at least one display panel, and wherein the illuminated portion of the display panel is at least 2 square cm.

3. The display of claim 1, wherein at least one display panel of the display changes color as a function of the changing operating state of the treatment device.

4. The display of claim 1, wherein a light source, in particular a color-neutral light source, supplies at least one display panel with light, whereby the display panel is colored or translucent and the light source is disposed behind the display panel.

5. The display of claim 1, wherein a plurality of light sources are provided for supplying the displays, which have at least partially different colors, and of which at least two supply the same display panel.

6. The display of claim 1, wherein the light source is covered by a cover that is translucent to the light emitted by the light source.

7. The display of claim 1, wherein at least one display panel of the display is kept colored and takes up a substantial part of a surface of the treatment device visible from the side or front.

8. The display of claim 7 wherein the substantial part of the surface is between at least two and approximately five percent.

9. The display of claim 1, wherein the display is disposed on the front side of the device and/or the display is disposed above the device and/or laterally on the device and/or on the underside.

10. The display of claim 1, wherein the color signals are constantly visible during the respective operating state and/or are visible in intervals.

11. The display of claim 1, wherein at least one display panel is color coated and at least two different color-coated display panels are alternatingly visible depending on the operating state of the treatment device.

12. The display of claim 1, wherein the display is connected spatially with the treatment device via a cable.

13. The display of claim 1, wherein the display is connected spatially with the treatment device via a radio.

14. The display of claim 1, wherein the device is a burning oven or kiln, or a compression oven, or a polymerization device that operates with light and/or heat.

15. The display of claim 1 wherein the display panel is comprised of a so-called black glass disk (acrylic glass with very fine incorporated soot particles), so that with all states of ambient light, the visibility is comparatively good; however still a corresponding display is realized in a cost-effective manner.

16. A display associated with a treatment device for dental material; the display being characterized by:
   the display being a function of at least one operating state of the device,
   the display incorporating one or more display panels which display different operating states of the treatment device exclusively with the assistance of color signals, wherein the color presented to the operator changes depending on the operating state of the treatment device, wherein the color signals appear on at least one colored display surface, which is disposed on a support element, and wherein the support element is controllably moveable in dependence on the operating state.

17. The display of claim 16, wherein the support element is formed by a rotary band, and wherein multiple colored surfaces with different colors are disposed on the rotary band.

18. The display of claim 16, wherein the support element is formed by a rotatable disk, and wherein multiple colored surfaces having different colors are disposed on the rotatable disk.

19. A display for displaying at least one operating state of a dental material treatment device by use of a plurality of colored signals, wherein each colored signal is associated with a unique operating state of the device, and wherein a color change is realized by switching off a light source having an emission spectrum corresponding to one color, and prompt switching on of a further having an emission spectrum corresponding to a different color.

20. A display for displaying at least one operating state of a dental material treatment device by using a plurality of colored signals, wherein the color presented to the operator changes depending on the operating state of the treatment device, wherein the color signals appear on at least one colored display surface, which is disposed on a support element, and wherein the support element is controllably moveable in dependence on the operating state.

21. A display associated with a treatment device for dental material; the display being characterized by;

the display incorporating one or more display panels which display different operating states of the treatment device exclusively with the assistance of color signals, each color being associated with, an operating state of the device, the color presented to the operator changing depending on the operating state of the treatment device, and means to change the color of at least one display panel of the display by switching off a light source having an emission spectrum corresponding to one color, and promptly switching on of a further light source having emission spectrum corresponding to a different color.

22. A display associated with a treatment device for dental material; the display being characterized by:

the display being associated with a dental material treatment device and displaying a function of at least one operating state of the device, the display incorporating one or more display panels which display different operating states of the treatment device exclusively with the assistance of color signals, wherein the color presented to the operator changes depending on the operating state of the treatment device, wherein the color signals appear on at least one colored display surface, which is disposed on a movable support element, and wherein the support element is controllably moveable in dependence on the operating state.

* * * * *

UNITED STATES PATENT AND TRADEMARK OFFICE
CERTIFICATE OF CORRECTION

PATENT NO. : 7,777,696 B2  Page 1 of 1
APPLICATION NO. : 11/318780
DATED : August 17, 2010
INVENTOR(S) : Gottfried Rohner et al.

It is certified that error appears in the above-identified patent and that said Letters Patent is hereby corrected as shown below:

Claim 19, line 5 of column 9, --light source-- should be inserted after --switching on of a further--.

Signed and Sealed this

Ninth Day of November, 2010

David J. Kappos
*Director of the United States Patent and Trademark Office*